United States Patent [19]

Blunck

[11] 4,199,683

[45] Apr. 22, 1980

[54] ZERO-STABLE NONDISPERSIVE GAS ANALYZER

[76] Inventor: Otto H. Blunck, Trelleborgallee 2, 2400 Lubeck-Travemunde, Fed. Rep. of Germany

[21] Appl. No.: 936,062

[22] Filed: Aug. 23, 1978

[30] Foreign Application Priority Data

Nov. 3, 1977 [DE] Fed. Rep. of Germany ....... 2749229

[51] Int. Cl.$^2$ .............................................. G01J 1/00
[52] U.S. Cl. ................................................. 250/345
[58] Field of Search ........................ 250/343, 344, 345

[56] References Cited

U.S. PATENT DOCUMENTS

| 3,725,702 | 4/1973 | Schaefer | 250/345 |
| 3,968,369 | 7/1976 | Luft | 250/345 |

*Primary Examiner*—Alfred E. Smith
*Assistant Examiner*—Carolyn E. Fields
*Attorney, Agent, or Firm*—Roylance, Abrams, Berdo & Farley

[57] ABSTRACT

A nondispersive gas analysis device with minimal cross-sensitivity to interfering gases includes cuvettes for a sample gas and a reference gas which are irradiated by modulated infrared energy. Radiation which has passed through the cuvettes passes unidirectionally and successively through receiving chambers which are dimensioned to be geometrically and optically alike. The chambers are coupled through conduits to a pressure responsive differential signal generator unit. Loss of radiation intensity due to the window between two sets of receiving chambers is compensated for by using suitable optical coatings on the receiving chamber windows or by forming the walls of the upper set of chambers from a material having a thermal conductivity differing from that of the material used in the lower set. An absorption chamber positioned after the receiving chambers has an IR absorbing disc with a plurality of concentric grooves formed to define a sawtooth pattern. Embodiments for in-phase and out-of-phase use are disclosed.

23 Claims, 3 Drawing Figures

ZERO-STABLE NONDISPERSIVE GAS ANALYZER

This invention relates to a nondispersive gas analysis device having improved zero stability and good sensitivity.

BACKGROUND OF THE INVENTION

It is known to provide a nondispersive infrared gas analysis device with a sample container for a gas which is to be analyzed wherein the receiver arrangement is subdivided into two separate layers which are formed to contain the same fluid and which are penetrated successively by a beam of radiation after the beam has passed through the sample container and wherein the height, in the direction of passage of the radiation, of a first receiving chamber containing the first receiving layer is several times smaller than the height of a second receiving chamber containing the second receiving layer. The purpose of this construction is to obtain better stability whenever the gas mixture to be analyzed does not contain the gas component, the existence of which is to be determined. This is shown in German Patent No. 10 17 385.

As an improvement on this device, especially in the case of trace analysis, a further nondispersive infrared gas analysis device is known wherein two adjacent containers are provided, one to contain the mixture to be analyzed and the other to contain a reference substance. The apparatus also includes an arrangement for the production of two substantially identical counterphase modulated beams of rays which alternatingly pass through the mixture to be analyzed and the reference substance, and a single ray, two-layer receiver with two separate successive receiving two-layer receiver with two separate successive receiving chambers. As in the first case, this arrangement of the two successive receiving chambers lying in the path of rays also serves to achieve a sufficiently constant zero value, and is shown in German Patent No. 13 02 592.

Another known nondispersive infrared gas analysis device has a separate unidirectional path of the measuring and comparison rays and contains two receiving layers of variable length disposed in the same sequence successively in each path of rays and wherein both the energy difference between the absorbed energies of the receiving layers acted upon first by the radiation as well as the energy difference between the absorbed energies is formed in the receiving layers acted upon last by the radiation, and the corresponding electrical signals are then connected in opposition. This is shown in German Auslegeschrift No. 11 09 418.

Yet another nondispersive infrared gas analysis device includes separate paths for measuring and reference rays and includes two receiving chambers of variable length lying successively in each ray path. In this apparatus, the energy difference is determined between the pertinent sums of the absorbed energy of the receiving chamber acted upon first in one ray path and of the receiving chamber acted upon last in the other ray path. In this device, as in the previously described devices of the prior art, the purpose of the arrangement is to obtain an exact zero point, this being shown in German Auslegeschrift No. 16 98 218.

Finally, the prior art includes a nondispersive infrared gas analysis device with separate paths for measuring and reference-rays and with means for measuring the difference of the radiation energies absorbed in the receiving chambers. For the purpose of compensating for fluctuations in pressure, produced by shocks and accelerations of the mass of gas in the receiving chambers and their connecting lines, which fluctuations are superposed as interfering signals on the actual measuring signal, two additional gas filled chambers which are not acted upon by the radiation are provided, these chambers being assigned to the detector chambers in the paths for the measuring and comparison rays, the additional chambers being connected crosswise by gas conducting conduit. This is shown in U.S. Pat. No. 2,555,327.

The two layer receiving chambers used in these prior art gas analysis devices wherein the two receiving layers are penetrated by the radiation are dimensioned such that the receiving layer penetrated last by the radiation is longer than the receiving layer penetrated first by the radiation. With that relationship of the two layer receiving chambers, a particularly stable zero point results.

It has been found that although the devices of this type do have a satisfactory zero point character, they have the disadvantage of being "cross-sensitive" to interfering gases which almost always occur in practice in the gas to be measured or analyzed, the infrared absorption bands of which at least partly overlap those of the gas component for which the analysis is made. This interfering effect is decreased or softened to a degree in the known devices by the use of the receiving layers disposed in succession, but is not completely eliminated because of the variable lengths of the layers. This residual interference effect may make the use of the infrared gas analysis devices in some case, particularly where good selectivity is of importance, impossible. It has been known that the cross-sensitivity effect may be eliminated by suitable radiation filters. However, the use of such filters simultaneously reduces the sensitivity of the device. As a result of the amplification which must be increased when sensitivity is reduced, other interference effects gain in importance and, in addition, the filters show a considerable temerature effect. Moreover, the radiation filters add to the cost of the apparatus.

Even in these devices, zero-drifts may still occur, despite the basically good zero point character. In order to eliminate these zero-drifts, apparatus have been known by which the zero point is controlled and possibly automatically adjusted at certain intervals, either fixed or at intervals to be selected by the operator.

BRIEF DESCRIPTION OF THE INVENTION

It is an object of this invention to provide a nondispersive infrared gas analysis device using receiving chambers lying in succession in the path of the rays which exhibit improved behavior in regard to the interference by the infrared-active gases which can be present in the measuring gas and which especially diminishes the so-called "cross-sensitivity" effect to practically zero without impairing the stability and sensivity as compared with known devices.

A further object is to provide an apparatus in which the bodies enclosing the receiving chambers are constructed to be geometrically and optically practically identical so that both the front receiving chambers as well as the rear receiving chambers are developed identically. This identity not only includes the dimensioning of the chamber, but as to the optical identity, it includes identical provision of windows as to their number and construction. In one aspect, this means that the front chambers have a common front and rear window.

As a result, the advantages achieved with the invention are minimal cross-sensitivity of the device along with good zero point stability and sensitivity. The infrared gas analyzer of the invention is formed using, for the most part, only circularly formed parts and may thus be produced inexpensively. As a result of the compact construction, it is possible to achieve relatively small dimensions, and the device is rugged and the individual components are easily acceptable. As a result of the compact and symmetrical construction, the sensitivity to shock and the effects of temperature are slight.

In order that the manner in which the foregoing and other objects are attained in accordance with the invention can be understood in detail, particularly advantageous embodiments thereof will be described with reference to the accompanying drawings, which form a part of this specification, and wherein.

DETAILED DESCRIPTION OF THE INVENTION

Figure 1:
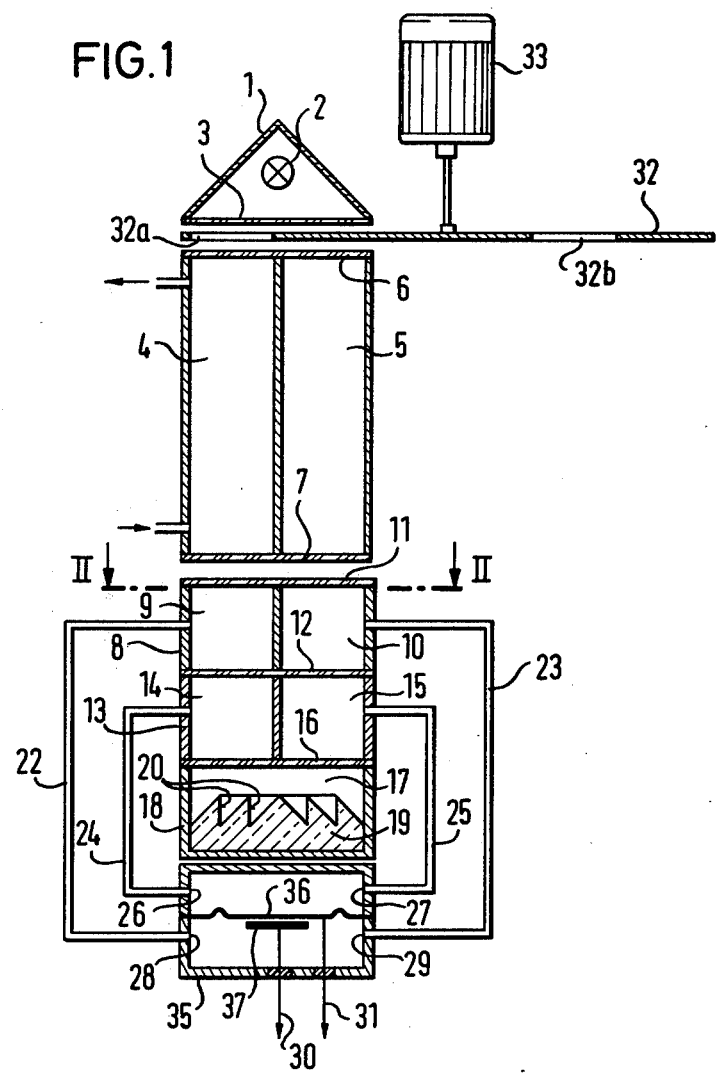
FIG. 1 is a schematic side elevation, in longitudinal section, of a nondispersive infrared gas analyzer with anti-phase modulation in accordance with the invention.
Figure 2:
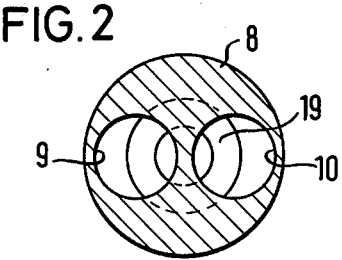
FIG. 2 is a transverse section along line 2—2 of FIG. 1.

As shown in FIG. 1, the apparatus of the invention includes a source of infrared radiation including a housing 1 and a radiation transparent window 3, the housing containing a thermal radiator 2. The radiation emanating from radiator 2 passes through window 3 and is modulated by a shutter wheel 32 driven by a motor 33. As schematically illustrated, disc 32 is provided with a plurality of openings 32a and 32b which are circularly spaced apart, alternating ones 32a of the openings being adjacent the periphery of the disc and the remaining openings 32b being radially inwardly thereof so that the modulation is permitted to pass therethrough in an anti-phase relationship, shifted by, for example, 180°. The beams of rays thus modulated in phase opposition are directed through a divided cuvette structure including a cuvette container 4 to contain the gas to be measured or analyzed and a cuvette container 5 for containing a reference gas. The radiation enters the cuvettes through a window 6, passes therethrough, and emerges through a window 7 and passes into a receiver arrangement which contains two front chambers 9 and 10 which are formed as circular bores in a cylindrical body 8, the shape and relationship of chambers 9 and 10 in body 8 being more clearly shown in FIG. 2. At the input end, chambers 8 and 9 are closed by a window 11 and the other ends of these chambers are closed by a rear window 12 in a manner as illustrated such that windows 11 and 12 cover up the entire ends of block 8. The surface of window 12 facing toward chambers 9 and 10 is suitably coated to provide a surface heat conductivity at least as great as the heat conductivity of the opposite surface which faces chambers 14 and 15.

The receiver arrangement further includes two additional chambers 14 and 15 which are formed in the same fashion as chambers 9 and 10 and are aligend respectively with those chambers. Chambers 9, 10, 14 and 15 are dimensioned so that they have a square cross section in a plane which passes through the axis of symmetry parallel with the direction of the radiation so that the length of each chamber is equal to its diameter. As a result of this arrangement, the formation and down lead of pressure pulses produced in the chambers by radiation absorption is favored. As a further result of the formation of the chambers as described, a compact close arrangement of the measuring chamber will be achieved. Thus, even slight temperature differences can be avoided in the measuring chamber arrangement. Such temperature differences could affect the absorption behavior in the chamber by way of impact broadening effects. The use of continuous windows 11 and 12, rather than using separate windows above each chamber, has the advantage of absolute symmetry of the structure. Although alternative arrangements are possible, the achievement of absolute symmetry in such arrangements is difficult because of the exceedingly precise relationship of components necessary. Thus, the one-piece construction is preferred.

At the rear or output end of body 13 containing chambers 14 and 15 is a window 16 which is formed in a manner similar to windows 11 and 12. The radiation passes through window 16 and enters a chamber 17 which contains a body 19 which is made from an infrared absorbing dielectric such as, for example, glass or a glass-like transparent plastic such as the polymethacrylates. Body 19 is formed in the shape of a circular disc and is provided in the face directed toward window 16 with a plurality of concentric grooves 20 which are formed such that a sawtooth-like pattern results in a transverse section through the center of the disc. It will be observed that one edge of each sawtooth extends parallel to the direction of radiation.

In chamber 17, all radiation passing through the window 16 from the receiving chambers is absorbed so that no portions of the radiation are reflected back again into the other chambers. This is enhanced by the geometrical shape of body 19 since the radiation which enters into chambers 17 must be reflected at least three times from body 19 before it can again enter into chambers 14 and 15. Thus, the probability of full absorption is great and any reflected radiation is practically zero. Thus, chamber 9, 10, 14 and 15 are subjected to radiation which is exclusively unidirectional.

Chamber 17 may also be formed in a manner such that a body of an infrared absorbing dielectric is disposed in it which consists of a casing fitted against the inner surface of body 18 and which has a centrally attached cone. In this variation the radiation must also be reflected at least three times before it can again enter chambers 14 and 15. Because of the multiple possibility of absorption, any radiation reflected back into the chambers 14 and 15 is without significance.

The absorptive action of chamber 17 may be further enhanced by the selection of a material for window 16 such that radiation incident thereon is strongly absorbed. Thus, a window of standard glass can be used for window 16. If the absorptive effect is sufficiently great, it is possible that chamber 17 can be omitted entirely.

Chamber 9 is connected through a conduit 22 to one side of a diaphragm capacitor unit 35 which contains a transverse flexible electrically conductive membrane 36 and a fixed electrode 37. Membrane 36 divides the chamber into two portions, conduit 22 being connected to one portion at 28. Similarly, chamber 10 is coupled through a conduit 23 to the same side of capacitor unit 35 at 29. Chamber 14 is coupled through a conduit 24 to the portion of capacitor unit 35 on the other side of membrane 36 at 26, and chamber 15 is coupled through conduit 25 to the same portion of the capacitor unit as chamber 14, at 27. As will be recognized, membrane 36 and electrode 37 form a capacitor, the value of which is a function of the spacing between those components. Thus, pressure differences between the two portion of unit 35 vary this spacing and permit the production of an electrical signal which appears on conductors 30 and 31 which are respectively connected to the fixed electrode and the membrane. These conductors can be connected to suitable conventional measuring equipment, not shown.

The goal of this device, of eliminating cross-sensitivities for interfering gases, is achieved by providing chambers of equal length, the chambers being disposed successively in the paths of the rays. When the gases are such that absorption occurs, which may be assumed in the case of many interfering gases to be in the overlap area of the band, there exists an approximately linear correlation between the thickness of the layers and the absorbed radiation energy. Therefore, whenever the lengths of the successive chambers are equal and the radiation between the chambers is not weakened, then the interfering effect, resulting from the overlapping of bands, is compensated. The radiation, however, is somewhat weakened by the window 12 disposed between the chambers 9 and 14 or 10 and 15. For that reason, the compensation of the interfering effects by successively placed receiving chambers of equal length is not exact. For an exact compensation, the signal of the rear receiving chamber must be increased by the amount which develops as a result of intensity weakening as a result of the window. According to the embodiment of FIG. 1, this is achieved by choosing the materials of blocks 8 and 13 such that they have different heat conductivities. Thus, the material of block 13 can be chosen to be steel and that of block 8 to be aluminum so that the walls of the chambers 14 and 15 have a lower heat conductivity than the walls defining chambers 9 and 10. The material used for block 13 can conveniently be a nickel chromium steel such as V2A-steel or V4A-steel which are special steels commonly referred to as V-steels.

In employing this arrangement of dimensions and materials, the fact is used that the level of the pressure pulse developing in a chamber as a result of radiation absorption is determined, among other things, by the heat conductivity of the walls enclosing the chamber. When the heat conductivity is lower, the pressure impulse is higher. Thus, the loss of intensity due to window 12 can be compensated.

Additional possibilities for increase of the pressure pulses in chambers 14 and 15 consist in the use of windows 11, 12 and 16 which have different surface heat conductivities which can be obtained generally by suitable coating. Thus, for example, all three windows 11, 12 and 16 can be provided with coatings such that they have heat conductivities which differ from each other. Alternatively, the windows 11 and 16 can be coated to have different heat conductivities from each other, in which case window 11 would be provided with a higher heat conductivity than window 16.

As a result of the conduit connections between chambers 9, 10, 14 and 15 as described, the differences in intensity of successive chambers 9 and 14 or 10 and 15 is always formed in phase opposition. This results, for one thing, in a stable zero point. It is true that this zero is not stable to the same degree as in the case of a known arrangement wherein the rear chamber is longer than the front one. Nevertheless, the zero point is still sufficiently stable for many applications. On the other hand, however, the cross-sensitivity is considerably improved as compared to known arrangement, and this is a decisive factor in this connection.

Figure 3:
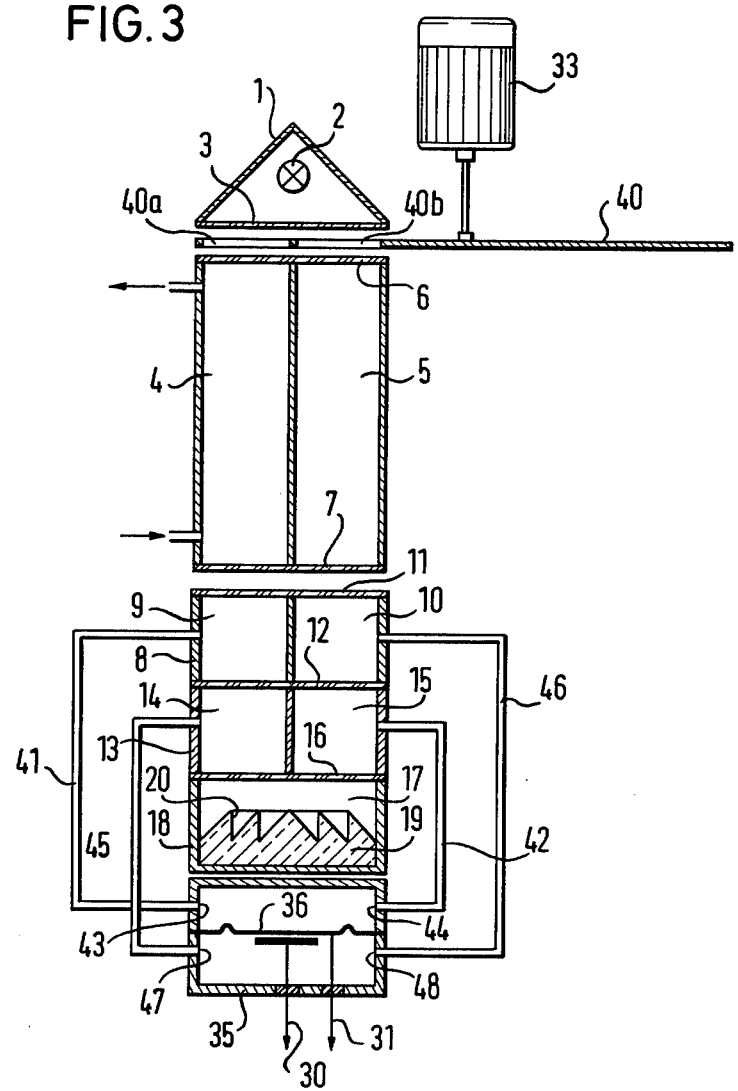
FIG. 3 is a schematic side elevation, in longitudinal section, of a further embodiment of a gas analyzer in accordance with the invention for in-phase modulation.

The apparatus in accordance with the invention can also be modified for use with the other form of modulation customary in infrared gas analysis devices wherein the radiation is supplied "in-phase" to the cuvettes. An embodiment for this purpose is illustrated in FIG. 3 wherein those components which are the same as illustrated in FIG. 1 are identified by the same reference numerals and will not be again described. In the embodiment of FIG. 3, the modulation disc is a disc 40 which is provided with openings 40a and 40b aligned along a radius of the disc. Thus, the openings arrive between the radiation source and cuvettes 4 and 5 at the same time and irradiate those cuvettes in an "in-phase" manner. In this arrangement it is also necessary to change the connections between the receiving chambers and the capacitor unit such that chambers 9 and 15 are coupled by conduits 41 and 42, respectively, to the same portion of condensor unit 35 as shown at 43 and 44, respectively. Also, chambers 14 and 15 are coupled to the opposite side of membrane 36 by conduits 45 and 46, respectively, at 47 and 48.

As will also be recognized, the modulation of the radiation can be accomplished by the technique of applying electrical pulses to the radiation source when in-phase operation is to be used. Other than these modifications, the structure, materials, coatings and the advantages of the in-phase version correspond to those of the anti-phase version.

It will also be recognized that although the invention has been described in connection with the use of a diaphragm capacitor arrangement as a means for the formation of the differential signals from the individual signals produced as a result of radiation absorption in the receiving chambers, it will be recognized that the invention may also be used in connection with other transducing means such as, for example, thermoelectric sensors.

While certain advantageous embodiments have been chosen to illustrate the invention, it will be understood by those skilled in the art that various changes and modifications can be made therein without departing from the scope of the invention as defined in the appended claims.

It should be noted that the coating of the windows 11, 12 and 16 may be made by a well known technology e.g. by metallizing, cathodic sputtering or evaporating or the like.

What is claimed is:

1. A nondispersive infrared gas analysis device comprising the combination of
    first and second gas-containing cuvettes adapted, respectively, to contain a gas to be analyzed and a reference gas, said cuvettes having radiation transparent means at both ends thereof;
    a source of radiation coupled to said transparent means at one end of the cuvettes to pass radiation thereto;
    receiver means at the other end of said cuvettes for receiving radiation emanating from said cuvettes, said receiver means comprising
    a first body;

means for defining first and second reception chambers in said first body adapted to receive radiation from said first and second cuvettes, respectively;

a second body;

means defining third and fourth reception chambers in said second body, said third and fourth chambers being aligned with said first and second chambers and said cuvettes so that radiation can pass serially along one path through said first cuvette and said first and third chambers and along another path through said second cuvette and said second and fourth chambers;

window means for covering the ends of said reception chambers and for separating said first and second chambers from said third and fourth chambers; and infrared absorption means at the output end of said third and fourth chambers to cause the radiation along said paths to be substantially unidirectional;

differential signal generating means for producing an electrical signal representative of the difference in radiation absorption in said reception chambers along said paths; and means for coupling said reception chambers to said differential signal generating means;

and wherein said first and second bodies are formed from materials having different thermal conductivity characteristics.

2. A device according to claim 1 wherein said means defining an absorption chamber includes a metallic casing having a recess to define said chamber, and an infrared absorbing body in said recess, said absorbing body being made from glass or transparent polymethacrylate.

3. A device according to claim 2 wherein said first body is physically closest to said cuvettes and is formed from a material having a higher thermal conductivity than said second body.

4. A device according to claim 2 wherein said first body is made of aluminum and said second body is made of steel.

5. A device according to claim 1 wherein the geometric and optical configurations of said first and second bodies are substantially identical.

6. A device according to claim 5 wherei said source of radiation includes modulating means for alternately irradiating said first and second cuvettes in a sequence of pulses of radiation.

7. A device according to claim 3 wherein said differential signal generating means includes a cavity having a movable diaphragm separating the cavity into two portions, the diaphragm having an electrically conductive member movable therewith;

a fixed electrode forming a capacitor with said conductive member;

circuit means for indicating the value of said capacitor as a function of diaphragm movement;

first conduit means interconnecting said first and second chambers and one portion of said cavity; and second conduit means interconnecting said third and fourth chambers and the other portion of said cavity.

8. A device according to claim 4 wherein each of said reception chambers has an axis of symmetry in the direction of travel of the radiation, and wherein each of said reception chambers has a square cross section in a plane containing the axis of symmetry.

9. A device according to claim 4 wherein said infrared absorption means includes an absorption chamber comprising a metallic body having a recess to define said chamber, and an infrared absorbing body in said recess, said body being formed as a disc having a plurality of concentric grooves in one face thereof, said grooves being formed to define a sawtooth pattern in transverse section with at least one edge of the sawtooth extending parallel with the direction of radiation.

10. A device according to claim 6 wherein said infrared absorbing body is glass.

11. A device according to claim 6 wherein said infrared absorbing body is polymethacrylate.

12. A device according to claim 6 wherein said window means includes a first single window member covering the input ends of said first and second chambers and a second single window member covering the output ends of said third and fourth chambers, said first member being coated to provide a greater surface heat conductivity than said second member.

13. A device according to claim 12 wherein said window means includes a third single window member separating said first and second chambers from said third and fourth chambers, said third member being coated to provide a surface heat conductivity different from said first and second members.

14. A device according to claim 6 wherein said window means includes first, second and third window members respectively covering the input ends of said first and second chambers, covering the output ends of said third and fourth chambers, and separating said first and second chambers from said third and fourth chambers, the surface of said third member facing said first and second chambers being coated to provide a surface heat conductivity at least as great as the surface thereof facing said third and fourth chambers.

15. A device according to claim 5 wherein said source of radiation includes modulating means for concurrently irradiating said first and second cuvettes in a sequence of pulses of radiation.

16. A device according to claim 15 wherein said differential signal generating means includes a cavity having a movable diaphragm separating the cavity into two portions, the diaphragm having an electrically conductive member movable therewith;

a fixed electrode forming a capacitor with said conductive member;

circuit means for indicating the value of said capacitor as a function of diaphragm movement;

first conduit means interconnecting said first and fourth chambers and one portion of said cavity; and second conduit means interconnecting said second and third chambers and the other portion of said cavity.

17. A device according to claim 16 wherein each of said reception chambers has an axis of symmetry in the direction of travel of the radiation, and wherein each of said reception chambers has a square cross section in a plane containing the axis of symmetry.

18. A device according to claim 16 wherein said nfrared absorption means includes an absorption chamber comprising a metallic body having a recess to define said chamber, and an infrared absorbing body in said recess, said body being formed as a disc having a plurality of concentric grooves in one face thereof, said grooves being formed to define a sawtooth pattern in transverse section with at least one edge of the sawtooth extending parallel with the direction of radiation.

19. A device according to claim 15 wherein said infrared absorbing body is glass.

20. A device according to claim 15 wherein said infrared absorbing body is polymethacrylate.

21. A device according to claim 15 wherein said window means includes a first single window member covering the input ends of said first and second chambers and a second single window member covering the output ends of said third and fourth chambers, said first member being coated to provide a greater surface heat conductivity than said second member.

22. A device according to claim 21 wherein said window means includes a third single window member separating said first and second chambers from said third and fourth chambers, said third member being coated to provide a surface heat conductivity different from said first and second members.

23. A device according to claim 15 wherein said window means includes first, second and third window members respectively covering the input ends of said first and second chambers, covering the output ends of said third and fourth chambers, and separating said first and second chambers from said third and fourth chambers, the surface of said third member facing said first and second chambers being coated to provide a surface heat conductivity at least as great as the surface thereof facing said third and fourth chambers.

* * * * *